United States Patent [19]

Tam

[11] Patent Number: 5,767,097
[45] Date of Patent: Jun. 16, 1998

[54] SPECIFIC MODULATION OF TH1/TH2 CYTOKINE EXPRESSION BY RIBAVIRIN IN ACTIVATED T-LYMPHOCYTES

[75] Inventor: Robert C. Tam, Costa Mesa, Calif.

[73] Assignee: ICN Pharmaceuticals, Inc., Costa Mesa, Calif.

[21] Appl. No.: 590,449

[22] Filed: Jan. 23, 1996

[51] Int. Cl.$^6$ .................. A61K 31/495; C07H 19/167
[52] U.S. Cl. ................... 514/43; 514/2; 514/46; 514/23; 514/27; 536/29.1; 536/28.6; 536/28.7
[58] Field of Search .................. 514/2, 43, 46, 514/23, 27; 536/29.1, 28.6, 28.7

[56] References Cited

U.S. PATENT DOCUMENTS 5,290,540  3/1994  Prince et al. .................. 424/45

OTHER PUBLICATIONS

Romagnani, Int. Arch. All. Immuno. (1992) vol. 98(4): pp. 279–285.
De Carli, et al. Autoimmunity (1994) vol. 18(4): pp. 301–308.
Racke, et al. J. Eypt). Med. (1994) Vol. 180(5): pp. 1961–1966.
Tarazona, et al. J. Immunol. (1995) vol. 154(2): pp. 861–870.
Yi, et al. J. Neuroimmuno. (1994) vol. 50(2) pp. 177–186.
McLachlan, et al. J. Clin. Endocrin. Metab. (1994) vol. 78(5) pp. 1070–1074.
Fox et al. J. Immunol. (1994) vol. 152(11): pp. 5532–5539.
Nabors, et al. Proc. Nat'l. Acad. Sci. USA (1995) vol. 92(8): pp. 3142–3146.
Chen et al Yaoxue Xeebao (1995) vol. 30(6): pp. 417–421.
Erard et al Challenges Mod. Med. vol. 8: pp. 43–48 (1994).
Klassen et al Science vol. 195(4200): pp. 787–789.
Jolley and Suchil, 1984, Clinical Applications of Ribavirin: pp. 93–96.
Marquardt et al, 1987, *J Pharmacol Exp Therapeutics* 240: 145–149.

*Primary Examiner*—Stephen Walsh
*Assistant Examiner*—Daryl Basham
*Attorney, Agent, or Firm*—Crockett & Fish

[57] ABSTRACT

Ribavirin is administered to a patient in a dosage range which is effective to modulate lymphokine expression in activated T cells. In particular, ribavirin is used to suppress Th2-mediated T cell responses and promote Th1-mediated T cell response. Thus, instead of administering ribavirin in its well-recognized role as an anti-viral agent, ribavirin is herein used in the treatment of imbalances in lymphokine expression. Such imbalances may be found to be concomitants of allergic atopic disorders such as allergic asthma and atopic dermatitis, helminth infection and leishmaniasis, and various primary and secondary immunodeficiencies, which may or may not also be associated with viral infection.

9 Claims, 5 Drawing Sheets

SPECIFIC MODULATION OF TH1/TH2 CYTOKINE EXPRESSION BY RIBAVIRIN IN ACTIVATED T-LYMPHOCYTES

FIELD OF THE INVENTION

The field of the invention is immunology.

BACKGROUND OF THE INVENTION

The lymphokines are a group of polypeptides belonging to the family of cytokines, i.e. hormone-like molecules that can affect various cell functions and enable communication between different cells. Recent developments have helped to clarify the role of lymphokines in the immune response. Lymphokine production by helper $CD4^+$ (and also in $CD8^+$) T cells frequently fall into one of two phenotypes, Th1 and Th2, in both murine and human systems (Romagnani, 1991, *Immunol Today* 12: 256–257, Mosmann, 1989, *Annu Rev Immunol*, 7: 145–173). Th1 cells produce interleukin 2 (IL-2), tumor necrosis factor (TNFα) and interferon gamma (IFNγ) and they are responsible primarily for cell-mediated immunity such as delayed type hypersensitivity. Th2 cells produce interleukins, IL-4, IL-5, IL-6, IL-9, IL-10 and IL-13 and are primarily involved in providing optimal help for humoral immune responses such as IgE and IgG4 antibody isotype switching (Mosmann, 1989, *Annu Rev Immunol*, 7: 145–173).

Strongly polarized Th1 and Th2 responses not only play different roles in protection, they can promote different immunopathological reactions. Th1-type responses are involved organ specific autoimmunity such as experimental autoimmune uveoretinitis (Dubey et al, 1991, *Eur Cytokine Network* 2: 147–152), experimental autoimmune encephalitis (EAE) (Beraud et al, 1991, *Cell Immunol* 133: 379–389) and insulin dependent diabetes mellitus (Hahn et al,1987, *Eur J Immunol* 18: 2037–2042), in contact dermatitis (Kapsenberg et al, *Immunol Today* 12: 392–395), and in some chronic inflammatory disorders. In contrast Th2-type responses are responsible for triggering allergic atopic disorders (against common environmental allergens) such as allergic asthma (Walker et al, 1992, *Am Rev Resp Dis* 148: 109–115) and atopic dermatitis (van der Heijden et al, 1991, *J Invest Derm* 97: 389–394), are thought to exacerbate infection with tissue-dwelling protozoa such as helminths (Finkelman et al, 1991, *Immunoparasitol Today* 12: A62–66) and Leishmania major (Caceres-Dittmar et al, 1993, *Clin Exp Immunol* 91: 500–505), are preferentially induced in certain primary immunodeficiencies such as hyper-IgE syndrome (Del Prete et al, 1989, *J Clin Invest* 84: 1830–1835) and Omenn's syndrome (Schandene et al, 1993, *Eur J Immunol* 23: 56–60), and are associated with reduced ability to suppress HIV replication (Barker et al, 1995, *Proc Soc Nat Acad Sci USA* 92: 11135–11139).

Thus, it is clear that modulation of the lymphokine profiles of the aforementioned disease states would be of therapeutic benefit. Promoting a Th1 response would most likely lead to the reversal of a Th2 phenotype and vice versa. Monoclonal antibodies (mAb) to lymphokines, lymphokines themselves and other agents such as thiol antioxidants (Jeannin et al, 1995, *J Exp Med* 182: 1785–1792) have been shown to reverse the pathogenesis of certain diseases by inhibiting the disease-promoting cytokine pattern, either Th1 or Th2. For example, intracellular protozoan infections are limited by IFNγ but exacerbated by IL-4, while nematode infections are controlled by IL-4 and exacerbated by IFNγ (Heinzel et al, 1989, *J Exp Med* 162: 59–72, Else et al, 1994, *J Exp Med* 179: 347–351). Insulin-dependent diabetes mellitus in NOD mice and EAE in mice and rats can be ameliorated by treatment with IL-4 or anti-IFNγmAb before development of the disease (Rapoport et al, 1993, *J Exp Med* 178: 87–99, Racke et al, 1994, *J Exp Med* 180: 1961–1966, Campbell et al, 1991, *J Clin Invest* 87: 739–742). In addition, autoimmune graft versus host disease (GVHD) that is characterized by a systemic lupus erythrematosus-like syndrome is associated with Th2 lymphokine production and is inhibited by anti-IL-4 antibody (Umland et al, 1992, *Clin Immunol Immunopathol* 63: 66–73). On the other hand, Th1 cytokines are produced in acute GVHD, in which donor $CD8^+$ T cells develop into CTL and destroy the host immune system. Treatment with anti-IFNγ or anti-TNFα mAb ameliorates disease, and treatment with anti-IL-2 mAb converts acute GVHD to autoimmune GVHD (Via and Finkelman, 1993, *Int Immunol* 5: 565–572).

Clinical trials of native and recombinant IL-2 in treating HIV-infected patients have been in progress since 1983 (Volberding et al, 1987, *AIDS Res Hum Retroviruses*, 3: 115–124). Here, the relationship comes from the fact that development of AIDS has been reported to be associated with a shift in the pattern of lymphokines produced (Clerici and Shearer, 1994, *Immunol Today* 15: 575–581). Over time, in an infected individual progressing towards disease, a decreased expression of Th1 lymphokines such as IL-2 occurs (Maggi et al, 1987, *Eur J Immunol* 17: 1685–1690, Gruters et al, 1990, *Eur J Immunol* 20: 1039–1044, Clerici et al, 1993, *J Clin Invest* 91: 759–765), concomitant with an increased production of Th2 lymphokines such as IL4 and IL-10 (Clerici et al, 1994, *J Clin Invest* 93: 768–775, Hoffman et al, 1985, *Virology* 147: 326–335). T-cells from asymptomatic or long term survivors treated with IL-2 enhanced their anti-HIV activity whereas exposure to IL-4 or IL-10 reduced their ability to suppress HIV replication and to produce IL-2 (Barker et al, 1995, *Proc Soc Nat Acad Sci USA* 92: 11135–11139).

These current immunomodulatory therapeutics (mAbs and recombinant cytokines) are, however, not without limitations. For example with chronic monoclonal antibody treatment, the host animal develops antibodies against the monoclonal antibodies thereby limiting their usefulness. 'Humanized' monoclonal antibodies have been developed which apparently reduces the risk of an induced immune response to these mAbs. However, these are still under development, and in addition these new mAbs remain large proteins and therefore may have difficulty reaching there target sites. Cytokine-based therapeutics also have limitations. For example, IL-12 treatment of autoimmune GVHD leads to the development of acute GVHD in mice.

Ribavirin (1-β-D-ribofuranosyl-1,2,4-triazole-3-carboxamide) is a synthetic nucleoside capable of inhibiting RNA and DNA virus replication (Huffman et al, 1973, *Antimicrob. Agents Chemother* 3: 235, Sidwell et al, 1972, *Science* 177: 705). We have confirmed the observations of others who suggested that ribavirin, in addition to its antiviral activity, has an effect on certain immune responses (reviewed Jolley and Suchil, 1984, Clinical Applications of Ribavirin: p93–96). We have also confirmed observations of others that ribavirin affects the proliferation of mitogen- and antigen-activated T and B lymphocytes, (Tam et al, 1995 (data not shown), Peavy et al, 1980, *Infection and Immunity* 29: 583–589) and then when combined with cyclosporin, ribavirin showed efficacy in long term allograft survival , Jolley et al (1988, *Transplantation Proc* 20: 703–706).

In addition, we have significantly advanced the prior research by demonstrating that ribavirin modulates the cytokine pattern of an immune response at least in part by promoting a Th1 response and suppressing a Th2 response. In hindsight, this discovery is not inconsistent with prior research. First, ribavirin is known to inhibit both functional humoral immune responses, (Peavy et al. 1981, *J Immunol* 126: 861–864, Powers et al. 1982, *Antimicrob Agents Chemother* 22: 108–114) and IgE-mediated modulation of mast cell secretion (Marquardt et al. 1987, *J Pharmacol Exp Therapeutics* 240: 145–149, (both Th2 lymphokine-mediated events). Second, ribavirin antagonizes the antiviral effect of azidothymidine (AZT) in peripheral blood lymphocytes from HIV patients (Vogt et al. 1987, *Science* 235: 1376–1379). This finding is significant because AZT decreases IL-2 receptor (IL-2R) but not IL-2 expression (Viora and Camponeschi, 1995, *Cell Immunol* 163: 289–295). It is therefore possible that ribavirin antagonizes AZT by modulating IL-2 expression and elevating depressed levels of IL-2R. Third, ribavirin treatment of an immuno-compromised patient for chronic GVHD (a Th2-mediated disorder) led to a dramatic resolution of the disease, an outcome which did not occur with conventional immuno-suppressive therapies such as cyclosporin and glucocorticoids (Cassano, 1991, *Bone Marrow Transplantation* 7: 247–248). Finally, ribavirin treatment (one year) of patients for hepatitis C (HCV) revealed fewer lymphocyte aggregates and far less liver damage than placebo controls (Dusheiko et al. 1994, *Hepatology* 20: 206A). This observation may reflect the fact that although, the predominant immune response to hepatitis C is mediated by Th1 lymphokines, T cells of the Th0/Th2 phenotype can be infected by HCV (Zignego et al. 1994, unpublished data) and this infection may drive further antibody-mediated destruction of hepatocytes.

BRIEF DESCRIPTION OF THE DRAWINGS

TABLE 1 represents the resting and PMA/ionomycin-activated levels, at 48 and 72 h, of the lymphokines, IL-2, IL-4, TNFα and IFNγ (pg/ml) measured in extracellular supernatants and the cell surface expression of IL-2 (IL-2R) and IL-4 (IL-4R) receptors (mean channel fluorescence intensity) from human T cells.

SUMMARY OF THE INVENTION

Figure 1:
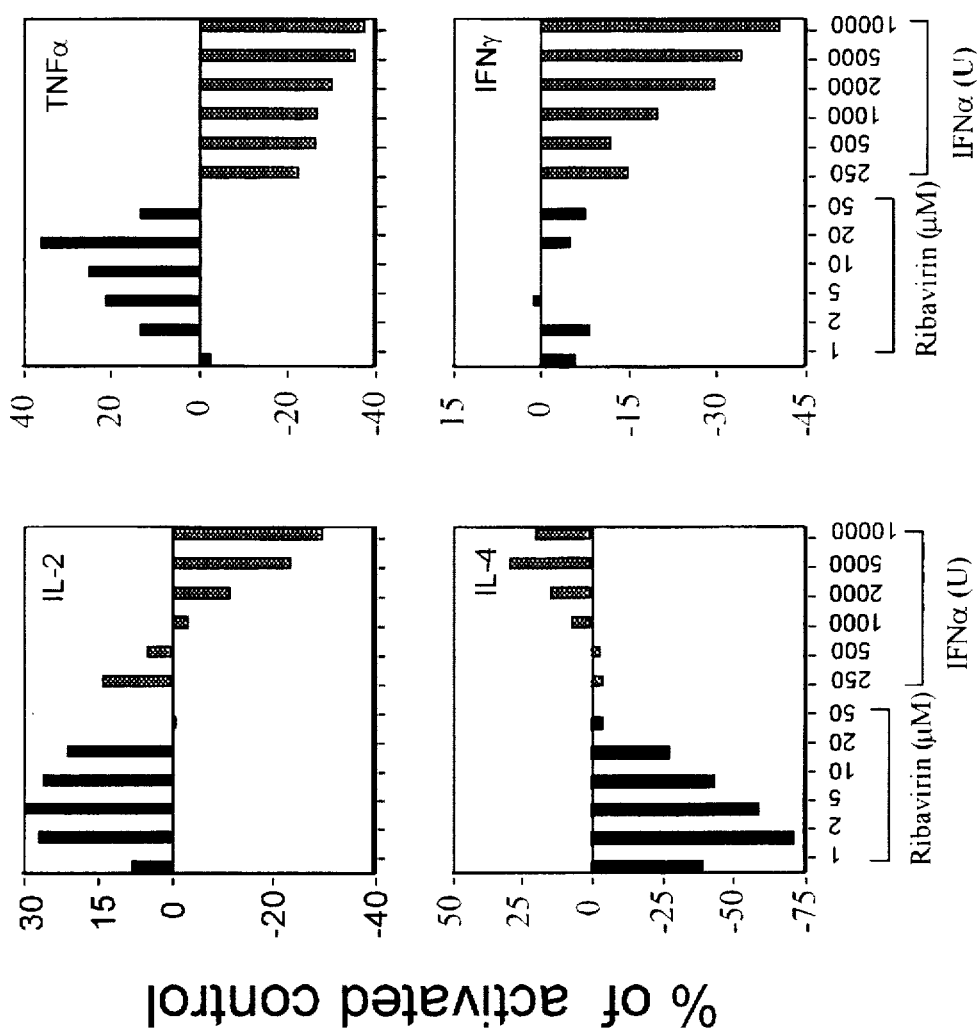
FIG. 1 is a graphical representation of the effect of ribavirin and interferon alpha on the extracellular expression of IL-2, IL-4, TNFα and IFNγ in PMA/ionomycin-activated T lymphocytes. Results are expressed as percentage of the increased lymphokine expression following PMA/ionomycin treatment alone.

In accordance with the present invention, the nucleoside, ribavirin, is administered to a patient in a dosage range which is effective to modulate lymphokine expression in activated T cells. In particular, ribavirin is used to suppress Th2-mediated T cell responses and promote Th1-mediated T cell response.

Thus, instead of administering ribavirin in its well-recognized role as an anti-viral agent, ribavirin is herein used in the treatment of imbalances in lymphokine expression. Such imbalances may be found to be concomitants of allergic atopic disorders such as allergic asthma and atopic dermatitis, helminth infection and leishmaniasis, and various primary and secondary immunodeficiencies, which may or may not also be associated with viral infection.

DETAILED DESCRIPTION OF SPECIFIC EMBODIMENTS

In a preferred embodiment, ribavirin is administered orally to a human patient in a dosage which achieves a blood serum level averaging 0.25–12.5 μg/ml, and most preferably, approximately 2.5 μg/ml. In a typical individuals, this optimimum serum level, works out to be approximately 4.5 mg/kg/day of body weight which can be administered in doses from 200–1200 mg. Preferably the dosages are divided into a number of smaller doses which are then administered throughout the day.

Since ribavirin has been on the market for several years, many dosage forms and routes of administration are known, and all appropriate dosage forms and routes of administration may be utilized. For example, in addition to oral administration, ribavirin may given intravenously, intramuscularly, intraperitoneally, topically, and the like, all of which are known. Pharmaceutical formulations comprising ribavirin may also comprise one or more pharmaceutically acceptable carrier, which may include excipients such as stabilizers (to promote long term storage), emulsifiers, binding agents, thickening agents, salts, preservatives, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the ribavirin, its use in the therapeutic compositions and preparations is contemplated. Supplementary active ingredients can also be incorporated into the compositions and preparations.

In addition to the therapeutic uses of the ribavirin contemplated herein, ribavirin may also be used as a laboratory tool for the study of absorption, distribution, cellular uptake, and efficacy.

EXAMPLES

Cell Lines And T Cell Purification

Peripheral blood mononuclear cells (PBMCs) were isolated from the buffy coat following Ficoll-Hypaque density gradient centrifugation of 60 ml blood from healthy donors. T-cells were then purified from the PBMCs using Lymphokwik lymphocyte isolation reagent specific for T-cells (LK-25T, One Lambda, Canoga Park Calif.). An average yield of 40–60×10⁶ T-cells were then incubated overnight at 37° C. in 20–30 ml RPMI-AP5 (RPMI-1640 medium (ICN, Costa Mesa, Calif.) containing 20 mM HEPES buffer, pH 7.4, 5% autologous plasma, 1% L-glutamine, 1% penicillin/ streptomycin and 0.05% 2-mercaptoethanol) to remove any contaminating adherent cells. In all experiments, T-cells were washed with RPMI-AP5 and then plated on 96-well microtitre plates at a cell concentration of 1×10⁶ cells/ml.

T-Cell Activation And Ribavirin Treatment

T-cells were activated by the addition of 500 ng ionomycin and 10 ng phorbol 12-myristate 13-acetate (PMA) (Calbiochem, La Jolla, Calif.) and incubated for 48–72 h at 37° C. PMA/ionomycin-activated T-cells were treated with 0.5–50 µM ribavirin or with 250–10000 U/ml of a control antiviral, interferon-alpha (Accurate, Westbury, N.Y.) immediately following activation and re-treated 24 h later. T-cells from each plate were used for immunofluorescence analysis and the supernatants used for extracellular cytokine measurements. Following activation, 900 µl cell supernatant from each microplate was transferred to another microplate for analysis of cell-derived cytokine production. The cells are then used in immunofluorescence analyses for intracellular cytokine levels and cytokine receptor expression.

Extracellular Cytokine Analyses

Cell-derived human cytokine concentrations were determined in cell supernatants from each microplate. Activation-induced changes in interleukin-2 (IL-2) levels were determined using a commercially available ELISA kit (R & D systems Quantikine kit, Minneapolis, Minn.) or by bioassay using the IL-2-dependent cell line, CTLL-2 (ATCC, Rockville, Md.). Activation -induced changes in interleukin-4 (IL-4), tumor necrosis factor (TNFα) interleukin-8 (IL-8) (R & D systems (Quantikine kit, Minneapolis, Minn.) and interferon-gamma (IFN-γ) (Endogen (Cambridge, Mass.) levels were determined using ELISA kits. All ELISA results were expressed as pg/ml and the CTLL-2 bioassay as counts per minute representing the IL-2-dependent cellular incorporation of ³H-thymidine (ICN, Costa Mesa, Calif.) by CTLL-2 cells.

Direct Immunofluorescence Studies (Cytokine Receptors)

For direct staining with fluorescence-conjugated antibodies to cell surface antigens, the cells were washed twice with isotonic saline solution, pH 7.4 (Becton Dickinson, Mansfield, Mass.) and resuspended in 50 µl isotonic saline solution and split into two samples. One sample aliquot was co-stained with either PE-anti CD25/FITC-anti CD4 or PE-rat anti mouse IgG+anti-CDw124/FITC-anti CD4 mAb and non-specific fluorescence was assessed by staining the second aliquot with PE/FITC-labeled isotype-matched control monoclonal antibody. All fluorescence-labeled monoclonal antibodies were obtained from Becton Dickinson (San Jose, Calif.) except for anti-CDw124 which was obtained from Pharmingen, San Diego, Calif. Incubations were performed at 4° C. in the dark for 45 min using saturating mAb concentrations. Unincorporated label was removed by washing in PBS prior to the analysis with a FACScan flow cytometer (Becton Dickinson).

Antigen density was indirectly determined in gated live CD4⁺ T cells and expressed as the mean channel of fluorescence (MCF). Surface expression of specific antigen (CDw124, CD25) was represented as the mean channel shift (MCS) obtained by subtracting the MCF of FITC- or PE-labeled isotype-matched (IgG1) control mAb-stained cells from the MCF of FITC- or PE-labeled antigen-specific mAb stained cells. Alternatively, surface expression of the CD4⁺-subset of cells stained with CD28 mAb was determined by subtracting the MCF of CD28⁺CD4⁺ from the MCF of CD28⁻CD4⁻ cells.

The viability of control untreated and ribavirin and interferon α-treated cells were determined in each batch of all oligonucleotides in multiple donors by staining with the vital dye, propidium iodide (5 µg/ml final concentration). The percentage of live cells which excluded propidium iodide was determined by flow cytometry and was >90% (range 90–99%) following treatment with all concentrations used.

Immunofluorescence Analyses of Intracellular Cytokine Expression

For analyses of the intracellular expression of IL-2 in CD4⁺ and CD8⁺T cell subsets, T cells were first treated for the last 4 h of 48–72 h activation with 10 µg Brefeldin A (Gibco BRL, Gaithersburg, Md.) to minimize secretion of newly synthesized IL-2 into the extracellular milieu. Following activation, 900 µl cell supernatant from each microplate was transferred to another microplate for analysis of cell-derived cytokine production. Prior to direct staining (30 min, 4 C, in the dark) with FITC-conjugated antibodies to the cell surface antigens, CD4 and CD8, the cells were washed twice with isotonic saline solution, pH 7.4 and resuspended in 100–150 µl Staining Buffer (phosphate buffered saline, pH 7.4 containing 1% Fetal Calf Serum (FCS) (Hyclone, Logan, Utah) and 0.1% sodium azide), and split into two samples. Stained cells were washed in 1 ml Staining Buffer and cell pellet resuspended in 100 µl Fixation Buffer (4% paraformaldehyde in PBS) following aspiration of the supernatant. Fixed cells were kept at 4 C for 20 mins, then washed in 1 ml Staining Buffer and cell pellet resuspended with mixing in 50 µl Permeabilization Buffer (0.1% saponin (ICN, Costa Mesa, Calif.) in PBS). Permeabilized cells were stained with PE-labeled IL-2 antibody for 30 min at 4 C in the dark and then washed in 1 ml Permeabilization Buffer, resuspended in 250 µl Staining Buffer prior to FACS analysis.

Analysis of Cytokine mRNA

Total RNA was extracted from resting T cells and from ribavirin and interferon α-treated and untreated activated T cells using a commercial variation of the guanidium thiocyanate/ phenol extraction technique (Trizol reagent (GIBCO/BRL). RNA was washed with 70% ethanol and finally resuspended in 10 µl DEPC-treated water.

cDNA synthesis reaction was performed as per manufacturers instructions (Promega, Madion, Wis.). Briefly, 1 µg of total RNA was heated at 65° C. for 10 min and cooled on ice before combining with 2 µl 10X reverse transcription buffer (100 mM Tris HCl (pH 8.8), 500 mM KCl, 1% Triton X-100), 5 mM MgCl, 2 µl 10 mM dNTPs (1 mM each dNTP), 0.5 µl RNase inhibitor, 1 µl oligo (dT)₁₅ primer (0.5 µg/µg RNA) and 0.65 µl AMV reverse transcriptase (H. C.). The reaction was incubated at 42° C. for 1 h followed by at 95° C. for 10 min and 5 min on ice.

The PCR reaction was performed using GeneAmp PCR kit (Perkin-Elmer Cetus, Foster City, Calif.). In a fresh tube, RT reaction mixture (3 µl) was combined with 5 µl 10×PCR buffer (500 mM KCl, 100 mM Tris-HCl, pH 8.3, 15 mM MgCl₂ and 0.01% (w/v) gelatin), 1 µl 10 mM dNTPs and 1 U of Taq DNA polymerase. The primers used were as follows: interleukin-2, interleukin-4, interferon-γ (human) primers (Stratagene, La Jolla, Calif.) and pHE7 ribosomal gene. Amplification conditions were 45 sec at 94° C., 1 min at 57° C. and 2 min at 72° C. for 35 cycles, followed by 8 min at 72° C. PCR products were analyzed on 2% agarose gel containing ethidium bromide. Following electrophoresis, PCR products were transferred to Hybond N+ membrane (Amersham, Arlington Heights, Ill.) in 20×SSC overnight and immobilized using 0.4M NaOH. Blots were hybridized with ³²P-γATP labeled oligonucleotide probes in Rapid-hyb buffer (Amersham) for 1 h at 42° C. Each cytokine primer mix was used as a radiolabeled probe (as per instructions). Equivalent loading was assessed following hybridization with a probe generated from pHE7 sense primer. Washed blots were then analyzed using PhosphorImager.

Effect of Ribavirin on Extracellular Cytokine Levels in Activated T Cells

Figure 2:
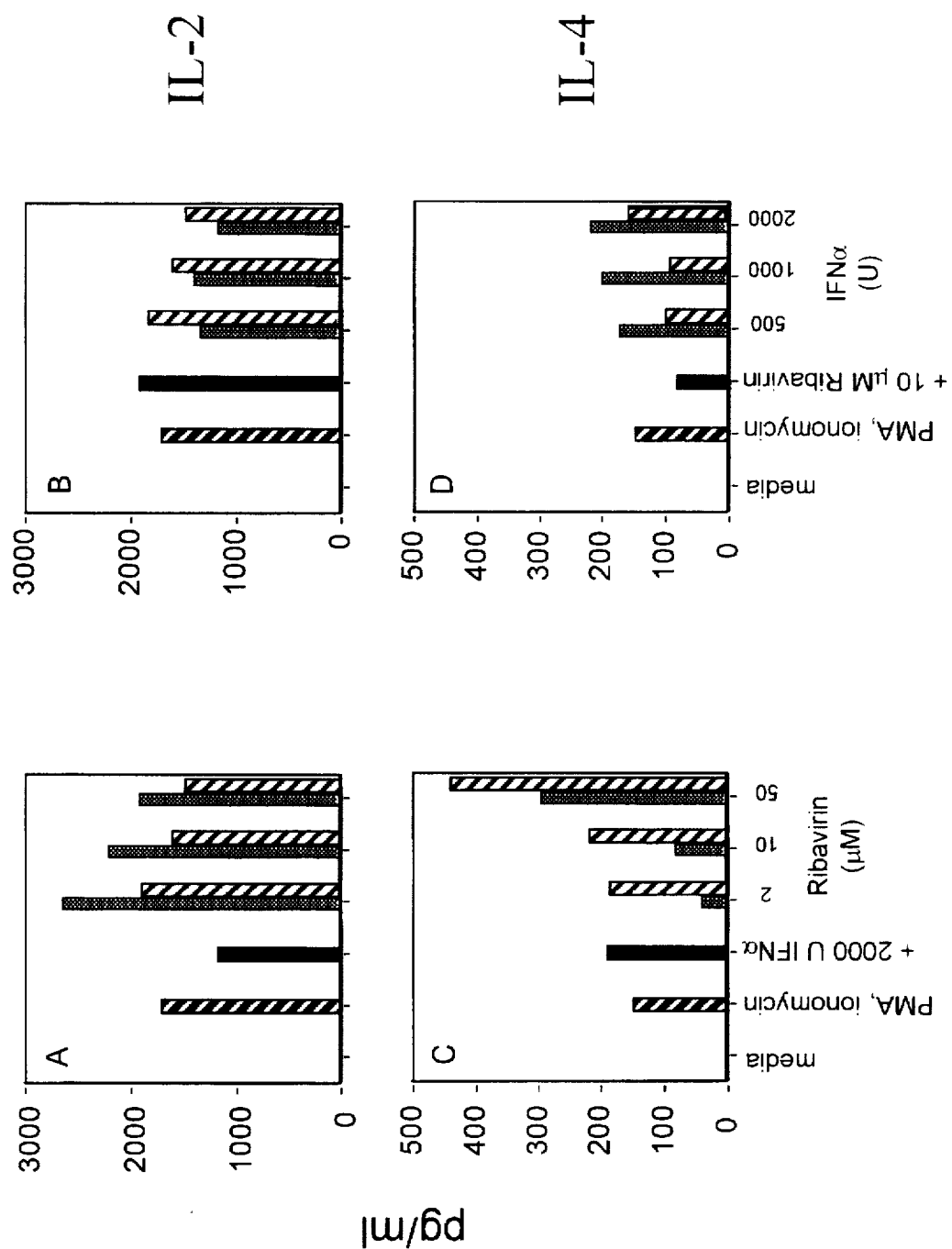
FIG. 2 is a graphical representation of the effect of 2, 10 or 50 μM ribavirin in the presence of 2000 U/ml interferon alpha (left panels) and the effect of 500, 1000 or 2000 U/ml interferon alpha (right panels)in the presence of 10 μM ribavirin on the extracellular expression of IL-2 (A and C) and IL-4 (B and D) in PMA/ionomycin-activated T lymphocytes.

PMA/ionomycin treatment (48–72 h) of human T-cells substantially increased the levels of all the cytokines analyzed i.e. IL-2, IL4, TNFα, IFNγ (Table 1). The first number in each cell depicts the arithmetic mean, and the numbers in parenthesis depicts the relevant ranges. N=4. In a representative experiment shown in FIG. 1, addition of ribavirin, in the dose range 0.5–50 μM, augmented activated levels of the Th1 cytokines, IL-2 and TNFα maximally at 5 μM (30%) and 20 μM (36%) respectively. In contrast, interferon-α, inhibited IL-2 and TNFα expression in a dose-dependent manner (range 250–10000 U/ml, maximal inhibition 33 and 38% respectively), when compared to levels in untreated activated T cells. In addition, ribavirin mediated a concomitant decrease in activated levels of the Th2 cytokine, IL-4 (peak inhibition of 74% at 2 μM) whereas interferon-α maximally increased extracellular IL-4 by 26% (10000 U/ml). Using combinations of ribavirin and interferon alpha, FIG. 2 shows that a constant 2000 U/ml of interferon alpha suppressed the ribavirin dose-dependent augmentation of activated IL-2 levels (A) and reversed the inhibition of activated IL-4 levels (C). Similarly, a constant 10 μM of ribavirin reversed the interferon alpha-mediated dose-dependent inhibition of activated IL-2 levels (B) and suppressed the augmentation of activated IL-4 levels (D).

Effect of Ribavirin on Cytokine mRNA Levels in Activated T Cells

Figure 3:
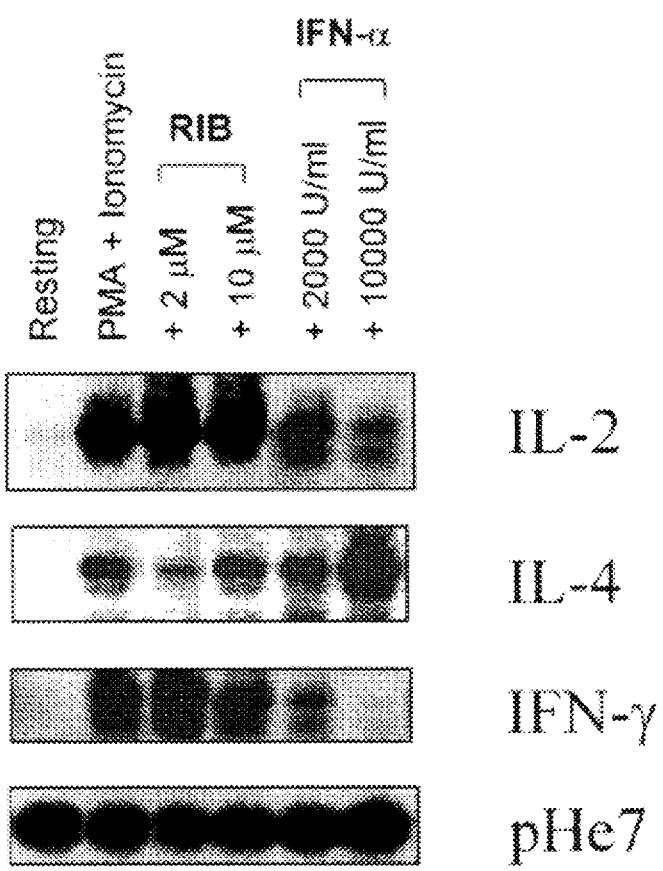
FIG. 3 is a graphical representation of the effect of ribavirin and interferon alpha on IL-2, IL-4 and IFNγ mRNA expression in PMA/ionomycin-activated T lymphocytes.
Figure 4:
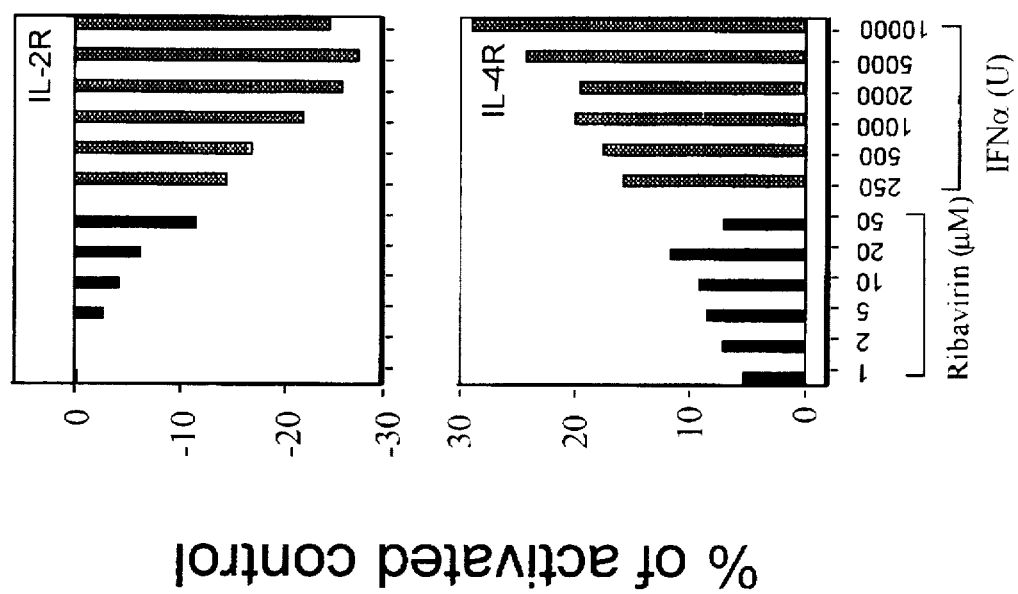
FIG. 4 is a graphical representation of the effect of ribavirin and interferon alpha on the cell surface expression of IL-2 and IL-4 receptors in PMA/ionomycin-activated T lymphocytes. Results are expressed as percentage of the increased lymphokine receptor expression following PMA/ionomycin treatment alone.

These opposing effects of ribavirin and interferon-α on activated extracellular cytokine levels were also observed at the level of transcription. FIG. 3 shows that PMA/ionomycin treatment of human T-cells substantially augments IL-2, IL-4 and IFNγ mRNA levels. Treatment with ribavirin (2, 5 and 10 μM) following T cell activation, elevates IL-2, decreases IL-4 and has no effect on IFNγ mRNA. In contrast, interferon α, at 1000, 2000 and 5000 U/ml decreases IL-2, increases IL-4 and decreases IFNγ mRNA. Therefore the respective dose-dependent effects of ribavirin and interferon α on IL-2, TNFα, and IL-4 mRNA expression paralleled the ELISA analyses. These data suggest that ribavirin promotes the synthesis of the Th1 cytokines, IL-2 and TNFα and inhibits the expression of the Th2 cytokine, IL-4 in activated human T cells Effect of Ribavirin on IL-2 and IL-4 Receptor Levels in Activated T Cells Using FACS analysis, we compared the effects of ribavirin and interferon α on expression of IL-2 (CD25) and IL4 (CDw124) receptor expression in activated T cells. PMA/ionomycin-treatment increases CD25 and CDw124 expression from resting levels of 50.16±0.45 and 62.31±1.46 to activated levels of 162.48±2.89 and 87.53±3.98 respectively (n=4). In a representative of 3 experiments, FIG. 4 show that ribavirin (1–50 μM) has little effect on activated levels of IL-2 and IL-4 receptor whereas interferon α, in the dose range 250–10000 U/ml, decreased IL-2 receptor and increased IL-4 receptor expression in a dose-dependent manner, when compared to receptor levels in control activated T cells. Therefore, these data show that the effect of ribavirin on cytokine synthesis acts independently of cytokine receptor expression. In contrast, the effect of interferon a treatment on IL-2 and IL-4 receptor correlates with that observed with its effect on activated IL-2 and IL-4 expression.

Figure 5:
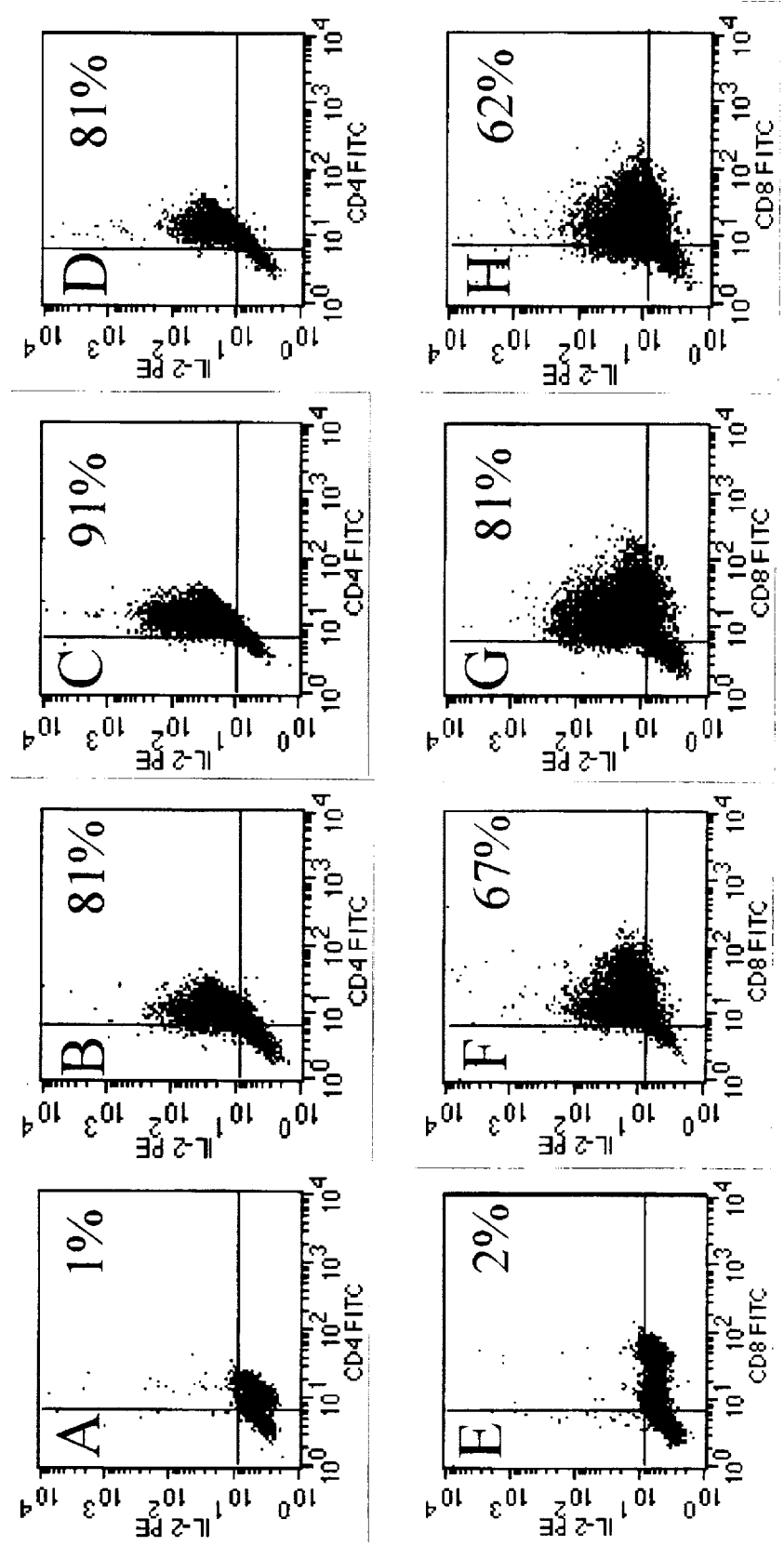
FIG. 5A–H is a graphical representation of the expression of intracellular IL-2 expression in resting (A and E) or activated CD4$^+$ (top panel) or CD8$^+$ (bottom panel) T cells treated with PMA/ionomycin alone (B and F) or in the presence of 10 μM ribavirin (C and G) or 5000 U/ml interferon alpha (D and H). Data from one experiment is shown and represented as the percentage of cells showing double positive staining for IL-2 and CD4 or CD8.

Effect of Ribavirin on Intracellular IL-2 Levels in CD4 and CD8+ Subsets of Activated T Cells We examined whether the effect of ribavirin on IL-2 expression was specific to CD4+ or CD8+ T cells. Intracellular IL-2 expression in fixed and Permeabilized activated T cells was determined by two-color flow cytometry using fluorescence-labeled antibodies to CD4 or CD8 and to IL-2. FIG. 5 shows that following treatment with ribavirin at 10 μM, the percentage of CD4+ T cells expressing IL-2 rose from 82 to 91% and the percentage of CD8+ expressing IL-2 increased from 81 to 91%. In contrast, the percentage of IL-2-expressing CD4+ and CD8+ cells following interferon-α-treatment (5000 U/ml) was 81 and 71% respectively. These data suggest ribavirin has an effect on intracellular IL-2 expression which does not discriminate between CD4+ or CD8+ T cell subsets. In contrast, interferon-α-treatment has little effect on CD4+ T cells and even reduces IL-2 expression in the CD8+ T cell subset.

TABLE 1

|  | 48 h Resting | 48 h Activated | 72 h Resting | 72 h Activated |
| --- | --- | --- | --- | --- |
| IL-2 | 6.7 | 1652 | 5.8 | 1462 |
|  | (5–9.3) | (848–2148) | (5–9.3) | (918–1866) |
| IL-4 | 7.5 | 209 | 8.5 | 131 |
|  | (7.1–8.2) | (81–363) | (7.2–9.2) | (121–148) |
| TNFα | 11.5 | 1573 | 8.3 | 1894 |
|  | (5–18) | (1474–1672) | (5–12) | (1240–2548) |
| IFNγ | 8.9 | 1285 | 9.3 | 2229 |
|  | (8.3–9.5) | (807–1765) | (9.1–9.4) | (1230–3228) |
| IL-2R | 50.1 | 163 | 60.1 | 163 |
|  | (40.6–59.7) | (160.9–166.5) | (49.8–70.4) | (160.1–165.5) |
| IL-4R |  |  | 52.3 | 77.7 |
|  |  |  | (42.6–59.2) | (73.5–82.1) |

What is claimed is:

1. A method of modulating Th1 and Th2 response in activated T cells of a human patient comprising administering Ribavirin to the T cells in a dosage which promotes the Th1 response and suppresses the Th2 response.

2. A method of treating a patient having a non-viral disease characterized by a cytokine profile in which Th1 response is suppressed and Th2 response is enhanced, comprising administering Ribavirin to the patient under a protocol which promotes the Th1 response and suppresses the Th2 response in the patient.

3. The method of claim 2 wherein the disease comprises an allergy.

4. The method of claim 2 wherein the disease comprises an autoimmune disease.

5. The method of claim 2 wherein the disease comprises a helminthic disease.

6. A method of treating a patient having a disease which includes a viral component and a non-viral component, the non-viral component being characterized by reduced Th1 levels and increased Th2 levels in activated T-lymphocytes, comprising administering Ribavirin to the patient under a protocol sufficient to promote the Th1 response and suppress the Th2 response in a patient.

7. The method of claim 6 wherein the disease involves primary immunodeficiency.

8. The method of claim 6 wherein the disease involves secondary immunodeficiency.

9. The method of claim 6 wherein the viral component involves the human immunodeficiency virus.

* * * * *